United States Patent

Thomas et al.

[11] Patent Number: 6,032,286
[45] Date of Patent: Mar. 7, 2000

[54] INNER ANKLE PROTECTOR DEVICE

[76] Inventors: Angela P. Thomas; Theresa Conner, both of 943 N. Humphrey, Oak Park, Ill. 60302

[21] Appl. No.: 09/135,455

[22] Filed: Aug. 17, 1998

[51] Int. Cl.[7] .................................................. A41D 13/00
[52] U.S. Cl. ..................... 2/22; 36/89; 36/130; 128/892; 602/65
[58] Field of Search ............................ 2/22, 911; 36/1.5, 36/89, 130; 128/892; 602/65; D29/120

[56] References Cited

U.S. PATENT DOCUMENTS

| | | | |
|---|---|---|---|
| 3,268,912 | 8/1966 | Whelan | 128/892 |
| 3,383,708 | 5/1968 | Pappas | 2/22 |
| 5,031,607 | 7/1991 | Peters | 128/80 H |
| 5,307,521 | 5/1994 | Davis | 2/22 |
| 5,507,720 | 4/1996 | Lampropoulos | 602/27 |
| 5,570,470 | 11/1996 | Miller | 2/22 |

*Primary Examiner*—Diana Oleksa
*Attorney, Agent, or Firm*—Henderson & Sturm LLP

[57] ABSTRACT

An inner ankle protector device 10 including a protector member 20 having an outer shell element 21 and an inner padded liner element 25 dimensioned to receive the user's inner ankle bone on one foot, a strap unit 12 including main 30 and auxiliary 33 strap members adapted to cooperate with one another and the protector member 20 to encircle the user's ankle and arch. The strap members 30, 33 also provide a thin, cushioned layer on the outside of the protector unit 11.

3 Claims, 1 Drawing Sheet

INNER ANKLE PROTECTOR DEVICE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of leg protectors in general, and in particular to an inner ankle protector device for bowlers.

2. Description of Related Art

As can be seen by reference to the following U.S. Pat. Nos. 5,031,607; 5,307,521; 5,507,720; and 5,570,470, the prior art is replete with myriad and diverse lower leg and ankle protector devices.

While all of the aforementioned prior art constructions are more than adequate for the basic purpose and function for which they have been specifically designed, they are uniformly deficient with respect to their failure to provide a simple, efficient, and practical protector device that is specifically designed and contoured to protect the user's inner ankle.

As many bowlers are all too painfully aware, there is a tendency for the bowling ball to come into contact with the inner ankle of the bowler's leading foot as the bowler is in the act of delivering the bowling ball down the bowling lane.

As a consequence of the foregoing situation, there has existed a longstanding need for a new type of ankle protector which is specifically designed and contoured to protect the inner ankle bone portion of the bowler's leading foot at the point of delivery of the bowling ball, and the provision of such a construction is a stated objective of the present invention.

BRIEF SUMMARY OF THE INVENTION

Briefly stated, the inner ankle protector device that forms the basis of the present invention comprises in general, a protector unit that is dimensioned and contoured to receive, cover, and protect the inner ankle bone on one of a user's feet and a strap unit which is provided to both operatively attach the protector unit to the user's person, but to also provide an additional cushioned layer to the exterior of the protector device.

As will be explained in greater detail further on in the specification, the protector unit comprises an outer generally rigid curved shell element provided with a padded liner element to cushion any impact that is imparted to the exterior surface of the shell element.

In addition, the exterior of the shell element is provided with a retaining strap that is dimensioned to receive an auxiliary strap member that is fixedly secured on one end to an ankle encircling main strap member wherein the main and auxiliary strap members comprise the strap unit.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
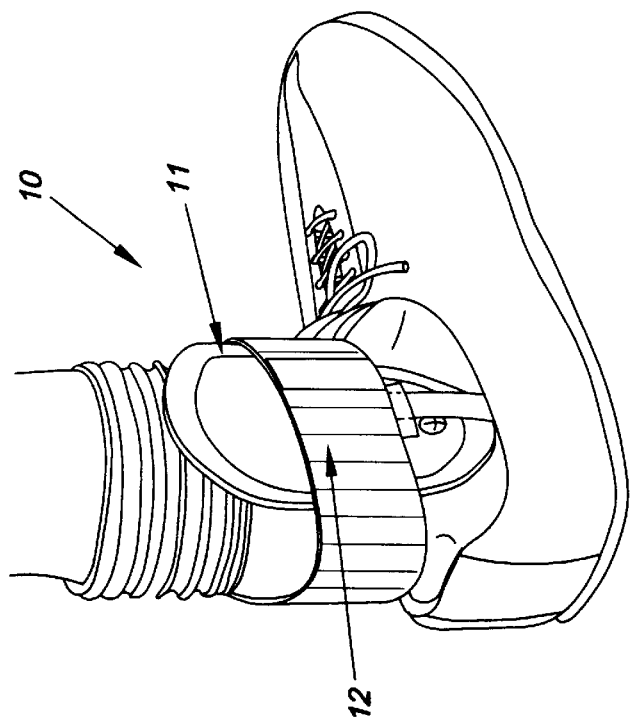
FIG. 1 is a perspective view of the ankle protector device deployed on the instep side of a bowler's ankle.

As can be seen by reference to the drawings, and in particularly to FIG. 1, the inner ankle protector device that forms the basis of the present invention is designated generally by the reference number 10. The device 10 comprises in general, a protector unit 11, and a strap unit 12. These units will now be described in seriatim fashion.

As can best be seen by reference to FIGS. 1 and 3, the protector unit 11 comprises a generally oval shaped contoured protector member 20 having a hard plastic outer shell element 21 having a concave interior surface 22 dimensioned to receive a user's inner ankle bone and a convex outer surface 23 provided with a transverse retaining strap 24 whose purpose and function will be described in greater detail further on in the specification.

In addition, the protector member 20 also includes a padded liner element 25 which is dimensioned to be received in the concave interior surface 22 of the plastic outer shell element 21 to provide cushioning for the user's inner ankle bone to reduce the effect of impact forces generated by a bowling ball (not shown) contacting the convex outer surface 23 of the shell element 21.

Figure 2:
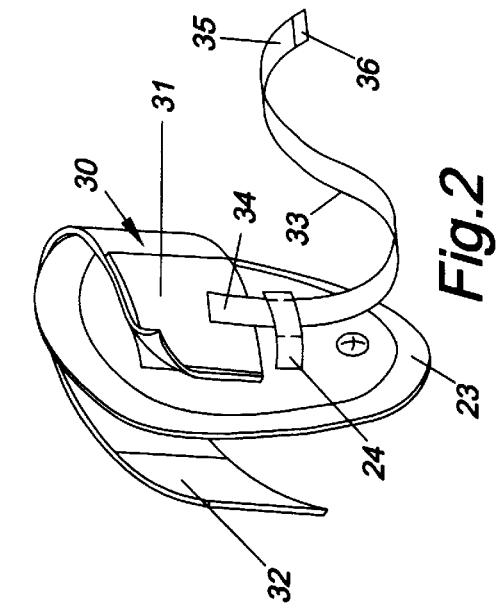
FIG. 2 is an isolated perspective view of the inner ankle protector device.
Figure 3:
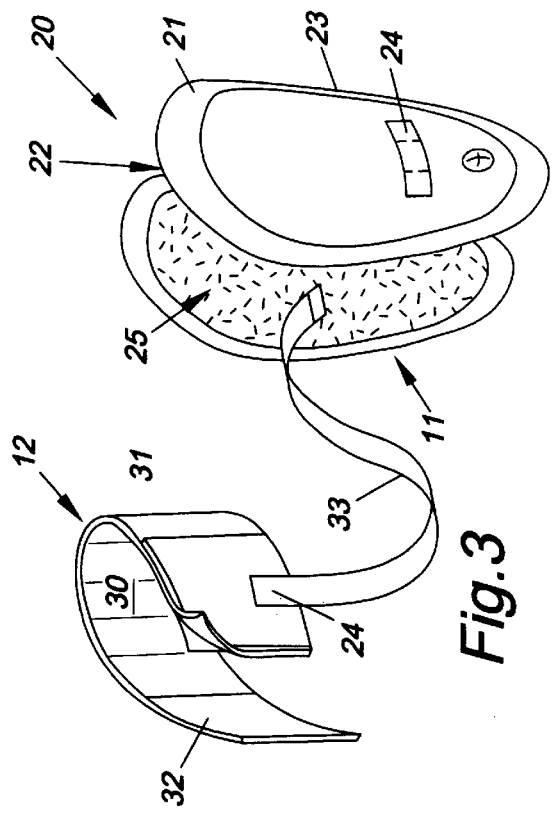
FIG. 3 is an exploded perspective view of the protector device.

Turning now to FIGS. 2 and 3, it can be seen that the strap unit 12 comprises in general: a relatively wide horizontally disposed main strap member 30 dimensioned to encircle a user's ankle and provided with cooperating hook and loop fasteners 31, 32 on its opposite ends, and a relatively slender vertically disposed auxiliary strap member 33 dimensioned to encircle the user's arch.

In addition, the auxiliary strap member 33 has one end 34 fixedly secured to one portion of the main strap member 30 and a free end 35 provided with a conventional fastener component 36 adapted to engage a cooperating fastener component (not shown) on another portion of the main strap member 30. The auxiliary strap member 33 cooperates with the main strap member to captively surround both the user's ankle and arch in a well recognized fashion.

As can also be appreciated by reference to FIGS. 2 and 3, the auxiliary strap member 33 is also dimensioned to be slidably received in the retaining strap 24 on the outer surface 23 of the plastic shell 21 to provide an operative engagement between the protector unit 11 and the strap unit 12.

Furthermore, as shown in FIG. 1, portions of the main 30 and auxiliary 33 strap members, as well as the retaining strap 24 also function to provide a thin cushioning layer on the outer surface 23 of the plastic shell 21 to further dampen any impact forces from a bowling ball (not shown) coming into contact with the exterior of the protector device 10.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

We claim:

1. An inner ankle protector device for protecting the inner ankle of a bowler wherein the device comprises:

a protector unit including a generally oval contoured protector member including a relatively hard outer shell element dimensioned to cover a user's inner ankle bone and an inner padded liner element; wherein said shell element has a concave inner surface and a convex outer surface;

a strap unit operatively associated with the protector unit and including a horizontally disposed main strap member and a vertically disposed auxiliary strap member which are adapted to cooperate with one another and the protector unit to encircle the user's ankle and arch wherein said convex outer surface of the protector member is further provided with a retaining strap which is dimensioned to receive a portion of said auxiliary strap member.

2. The device as in claim 1 wherein a portion of both said main strap and said auxiliary strap members and the retaining strap provide a thin cushioned layer on the outer surface of the shell element.

3. The device as in claim 2 wherein said auxiliary strap member has a captive end fixedly secured to one portion of the main strap member and a free end releasably engageable with another portion of the main strap member.

\* \* \* \* \*